United States Patent

Himmel et al.

[11] Patent Number: 5,432,075
[45] Date of Patent: Jul. 11, 1995

[54] LOW MOLECULAR WEIGHT THERMOSTABLE β-D-GLUCOSIDASE FROM ACIDOTHERMUS CELLULOLYTICUS

[75] Inventors: Michael E. Himmel, Littleton; Melvin P. Tucker, Lakewood; William S. Adney, Golden; Rafael A. Nieves, Lakewood, all of Colo.

[73] Assignee: Midwest Research Institute, Kansas City, Mo.

[21] Appl. No.: 275,995

[22] Filed: Jul. 15, 1994

Related U.S. Application Data

[63] Continuation-in-part of Ser. No. 125,115, Sep. 21, 1993, Pat. No. 5,366,884, which is a continuation-in-part of Ser. No. 826,089, Jan. 27, 1992, Pat. No. 5,275,944, which is a continuation-in-part of Ser. No. 412,434, Sep. 26, 1989, Pat. No. 5,110,735.

[51] Int. Cl.$^6$ ............ C12N 9/42; C12N 1/00
[52] U.S. Cl. ............................ 435/209; 435/822
[58] Field of Search ...................... 435/209, 822

[56] References Cited

U.S. PATENT DOCUMENTS

| | | | |
|---|---|---|---|
| 3,398,055 | 8/1968 | Bruno | 435/911 |
| 4,011,139 | 3/1977 | Horwath et al. | 435/210 |
| 4,081,328 | 3/1978 | Skinner et al. | 435/209 |
| 4,243,752 | 1/1981 | Skinner et al. | 435/209 |
| 4,610,965 | 9/1986 | Johnson et al. | 435/234 |
| 4,742,005 | 5/1988 | Yamanobe et al. | 435/99 |
| 4,945,053 | 7/1990 | Ito et al. | 435/209 |
| 4,966,850 | 10/1990 | Yu et al. | 435/200 |
| 5,110,735 | 5/1992 | Tucker et al. | 435/209 |
| 5,275,944 | 1/1944 | Himmel et al. | 435/209 |

OTHER PUBLICATIONS

Tucker et al., Biotechnology, vol. 7, Aug. 1989, pp. 817–820.
Seltzer, Chem. & Engin News, May 1987, pp. 23–24.
Mandels et al., 1969, Advan. Chem. Ser. 95, pp. 391–414.
Amelunxen et al., Mechanisms of Thermophily, Crit. Rev. Microbiol., 6, pp. 343–393, 1978.
Saddler et al., Can. J. Microbiol. vol. 27, pp. 288–294, 1981.
Mohaghegi et al. 1986, Int. J. System Bacteriol. 36:435–443.

Primary Examiner—David M. Naff
Assistant Examiner—Mike Meller
Attorney, Agent, or Firm—Edna M. O'Connor

[57] ABSTRACT

A purified low molecular weight β-D-glucosidase is produced from Acidothermus cellulolyticus ATCC 43068. The enzyme is water soluble, possesses activity against pNP-β-D-glucopyranoside, has a high of degree of stability toward heat, exhibits optimal temperature activity at about 65° C. at a pH range of from about 2 to about 7, has an inactivation temperature of about 80° C. at a pH range of from about 2 to about 7 and has a molecular weight of about 50.5–54.5 kD as determineded by SDS-PAGE.

5 Claims, 4 Drawing Sheets

LOW MOLECULAR WEIGHT THERMOSTABLE β-D-GLUCOSIDASE FROM ACIDOTHERMUS CELLULOLYTICUS

The United States Government has rights in this invention pursuant to Contract No. DE-AC. 36-83CH10093 between the United States Department of Energy and the Midwest Research Institute.

This application is a continuation-in-part of application Ser. No. 125,115, filed Sep. 21, 1993, now U.S. Pat. No. 5,366,884, which is a continuation-in-part of application Ser. No. 826,089, filed Jan. 27, 1992, now U.S. Pat. No. 5,275,944, which is a continuation-in-part of application Ser. No. 412,434, filed Sep. 26, 1989, now U.S. Pat. No. 5,110,735.

BACKGROUND OF THE INVENTION

1. Field of the Invention

The invention relates generally to a purification protocol for obtaining a low molecular weight, thermostable β-D-glucosidase from *Acidothermus cellulolyticus* The present application incorporates by reference the entirety of U.S. patent application Ser. No. 08/125,115. In particular, the invention pertains more specifically to a process for obtaining a low molecular weight, thermostable β-D-glucosidase from *Acidothermus cellulolyticus* culture broth or bacterium, submitted to the American Type Culture Collection under collection number 43068. The address where the *Acidothermus cellulolyticus* was deposited is 12301 Parklawn Drive, Rockville, Md. 20852.

Cellulose consists of long insoluble chains of covalently bonded glucose molecules, and in this condition, these long insoluble chains are too large to be transported through human and animal cell walls. However, through the agency of microorganisms, such as fungi and bacteria, enzymes known as cellulases are secreted, and these enzymes hydrolyze or depolymerize the cellulose into its monomeric component of glucose, which is a sugar that can be readily transported through the cell wall and metabolized.

The fermentable fractions of cellulosic biomass include cellulose (β-1,4-1inked glucose) and hemicellulose, a substantial heterogeneous fraction that is composed of xylose and minor five- and six-carbon sugars. Although it is an abundant biopolymer, cellulose is unique in that it is highly crystalline, insoluble in water, and highly resistant to depolymerization. The definitive enzymatic degradation of cellulose to glucose (the most desirable fermentation feedstock), is generally accomplished by the synergistic action of three distinct classes of enzymes: first, the "endo-1,4-β-glucanases" or 1,4-β-glucan 4-glucanohydrolases (EC 3.2.1.4), which act at random on soluble and insoluble 1,4-β-glucan substrates and are commonly measured by the detection of reducing groups released from carboxymethylcellulose (CMC); second, the "exo-1,4-β-glucosidases," including both the 1,4-β-glucan glucohydrolases (EC 3.2.1.74), which liberate D-glucose from 1,4-β-glucans and hydrolyze D-cellobiose slowly, and 1,4-β-D-glucan cellobiohydrolase (EC 3.2.1.91), which liberates D-cellobiose from 1,4-β-glucans; and third, the "β-D-glucosidases" or β-D-glucoside glucohydrolases (EC 3.2.1.21), which act to release D-glucose units from soluble cellodextrins and an array of glycosides. Synergistic actions of these three enzymes are necessary to completely depolymerize cellulose into glucose.

The synergistic reaction occurs as a result of a sequential, cooperative action among the three enzyme components in a complex in which the product of one enzyme reaction becomes the substrate for the next enzyme.

The development of economic processes for the conversion of low-value biomass to ethanol via fermentation requires the optimization of several key steps, especially that of cellulase production. This condition results from the extraordinarily high ratios of cellulase required to fully depolymerize cellulose. The problem is compounded by the relatively slow growth rates of cellulase producing fungi and the long times required for cellulase induction. However, the product of most cellulase systems is cellobiose, a dimer of glucose. Because cellobiose is almost universally inhibitory to cellulase enzymes, and because β-D-glucosidases convert cellobiose to glucose, the inclusion of β-D-glucosidases in processes where cellulases are used significantly enhances the effectiveness of the overall process of cellulose hydrolysis.

However, industrial processes utilizing cellulase enzymes such as β-D-glucosidase enzyme can be greatly improved and expanded by providing a β-D-glucosidase enzyme with increased thermal resistance for use in high temperature processes. Such resistance would also be useful to ensure increased stabilization resistance under other conditions known to denature enzymes, such as shear stress (from pumping), protease attack, and reduced contamination because they remain active at high process temperatures, which usually destroy other potentially contaminating enzymes.

THE PRIOR ART

Highly thermostable cellulase enzymes are known to be secreted by the cellulolytic thermophilic *Acidothermus cellulolyticus* gen. nov., sp. nov., a bacterium originally isolated from decaying wood in an acidic, thermal pool at Yellowstone National Park and deposited with the American Type Culture Collection (ATCC) under collection number 43068 (Mohagheghi et al. 1986, *Int. J. System. Bacteriol.* 36:435–443).

*Acidothermus cellulolyticus* is a unique thermophile and the cellulase complex produced by this organism is known to contain several different cellulase enzymes with maximal activities at temperatures of 75° C. to 83° C. In addition exhibiting the useful property of cellobiose (end product) inhibition resistance, the cellulases from *Acidothermus cellulolyticus* are active over a broad pH range centered about pH 5, the pH at which yeasts are capable of fermenting cellobiose and glucose to ethanol.

A high molecular weight cellulase isolated from growth broths of *Acidothermus cellulolyticus* was found by SDS-PAGE of approximately 156,600 to 203,400 daltons is described by U.S. Pat. No. 5,110,735.

A novel cellulase enzyme, known as the E1 endoglucanase and also secreted by *Acidothermus cellulolyticus* into the growth medium, is described in detail in the U.S. Pat. No. 5,275,944. This useful endoglucanase demonstrates a temperature optimum of 83° C. and a specific activity of 40 µM glucose release from caraboxymethylcellulose/min/mg protein. E1 endoglucanase was further identified as having an isoelectric pH of 6.7 and a molecular weight of 81,000 daltons by SDS polyacrylamide gel electrophoresis.

U.S. Pat. No. 4,081,328 disclose and describe general cellulase activities from *Thielavia terrestris*, which is an organism different from *Acidothermus cellulolyticus*. The cellulases described are incompletely characterized and no β-D-glucosidases are described at all.

U.S. Pat. No. 4,742,005 describes cellulases, and methods for using them. The cellulases are produced from a thermophilic organism called *Acremonium cellulolyticus* TN. This strain is not available from a US-based culture collection. The method in this patent produces a β-D-glucosidase found to have a pH range of 2 to 8, an optimum temperature of approximately 70° C., a Km of 3.40 on salicin, and a molecular weight of 240,000 daltons.

U.S. Pat. No. 5,110,735 disclose production of a thermostable, purified high molecular weight endoglucanase from *Acidothermus cellulolyticus*, wherein the endoglucanase has an optimum temperature for activity of about 65° C. at pH's from 2 to about 9. This reference provides no discussion of any β-D-glucosidase from the *Acidothermus cellulolyticus* organism.

A process for producing the α-1,6-glucosidase using thermophillic microorganisms is disclosed in U.S. Pat. No. 4,011,139. No temperature stability data is provided in this application.

U.S. Pat. No. 4,243,752 disclose production of increased yields of cellulolytic enzymes from *Thielavia terrestris*, and describes the separation and use of a β-D-glucosidase from *T. terrestris*. No temperature activity optimum of the β-D-glucosidase is provided, nor is there any other biophysical properties of the enzyme provided. The temperature optimum of the general cellulase complex is disclosed as being 60° C.

The production of thermostable xylanase and cellulase is disclosed in U.S. Pat. No. 4,966,850. The cellulases and xylanases are obtained from *Thermoascus aurantiacus*. While β-D-glucosidase activity was found in the culture supernatants, no biophysical characterization such as temperature pH optimum and molecular weight were determined, and the enzyme was not isolated.

Japanese Patent 63-109771 discloses the Bacillus sp KSM-635, and this organism produces a β-D-glucosidase-like enzyme of moderate thermostability. The enzyme has a temperature optimum of 40° C. and a molecular weight of 180,000 daltons.

SUMMARY OF THE INVENTION

In accordance with the present invention, it has been found that a low molecular weight, thermostable β-D-glucosidase enzyme isolated from the thermophillic bacterium *A. cellulolyticus* exhibits an activity optimum of about 65° C. on pNP glucoside.

The invention process for preparation of the low molecular weight, thermostable β-D-glucosidase enzyme is a purification process which is commenced by taking *Acidothermus cellulolyticus* strain 11B and maintaining this strain frozen at −70° C. after addition of about 77 μL of dimethyl-sulfoxide per mL of culture suspension.

The culture is prepared with an LPBM that contains $NH_4Cl$, $KH_2PO_4$, $Na_2HPO_4.7H_2O$, $MgSO4.7H_2O$, and $CaCl_2.2H_2O$, and this medium is supplemented with yeast extract D-cellobiose, and Wolin trace mineral solution Solka Floc BW-200 NF is used as the cellulosic substrate. All media are adjusted to about pH 5.2 and sterilized by autoclaving.

An aliquot of frozen culture is transferred to a shake flask. After incubation at about 55° C. with rotary agitation, an aliquot is transferred to a baffled shake flask containing the medium. After growth, the inocula is transferred to fermenters. The medium is maintained at pH 5.2 during fermentation by the addition of $NH_4OH$ and $H_3PO_4$, and dissolved oxygen is maintained at 40% of saturation by increasing the agitation rate and/or supplying pure oxygen as needed. The temperature is controlled at 55° C.

The inocula is then used to initiate growth in a fermenter with a large working volume. Control and growth conditions are identical to that used for the second stage inoculum fermentations in fermenters, except that the fermenter is harvested at 36 hours. Supernatant is freed from the cells by continuous centrifugation. The supernatant is then concentrated by a factor of about 20 using a hollow fiber ultraconcentrator, and the concentrated supernatant is stored at about 4° C.

In the purification step, the supernatant is further concentrated (5×) using ultrafiltration. The sample is dialyzed against 20 mM Tris buffer pH 8.0. An aliquot of this preparation is added to Tris buffer containing 1 M $(NH_4)_2SO_4$. The sample is loaded on an equilibrated Pharmacia Phenylsepharose FPLC column at room temperature. After the column is washed with 5 volumes of loading buffer, a reverse gradient (1.0M) in $(NH_4)_2SO_2$ is applied to the column. The β-D-glucosidase activity eluted from the column at 0% $(NH_4)_2SO_4$. The fractions showing activity is then dialyzed against 20 mM Tris pH 8.0 buffer and loaded on an equilibrated Pharmacia Q-Sepharose FPLC column. The column is washed with loading buffer for 5–8 column volumes and subjected to a normal NaCl gradient (0–0.5 M). The β-D-glucosidase activity is found to elute at a volume corresponding to a salt concentration of 650 mM NaCl. The enzyme eluted as a single, symmetrical peak, indicating a high level of homogeneity. These fractions are concentrated using an Amicon PM 10 membrane and loaded on a Pharmacia Superdex 75 size exclusion column. The purified protein is recovered from this column.

In accordance with a second aspect of the invention, the β-D-glucosidase obtained from the culture broth of *Acidothermus cellulolyticus* is subjected to SDS-PAGE and silver-staining to ascertain the molecular weight, which is approximately 52,500 daltons.

The enzyme aggregates in 20 mM acetate, 100 mM NaCl by size-exclusion chromatography. The temperature optima for a 30 minute incubation was found to be 65° C. The $K_m$ is determined by classical Michaelis-Menten kinetics to be 500 μM when pNP-β-D-glucoside is used as the substrate. This activity is equal to that of more commonly used enzymes such as the β-D-glucosidase from aspergillus-niger. The activity profile on 6 commonly studied p-nitrophenyl substituted substrates shows that this enzyme has the highest activity of pNP-glucopyranoside, and is clearly a β-D-glucosidase.

EXAMPLE I

Figure 1:
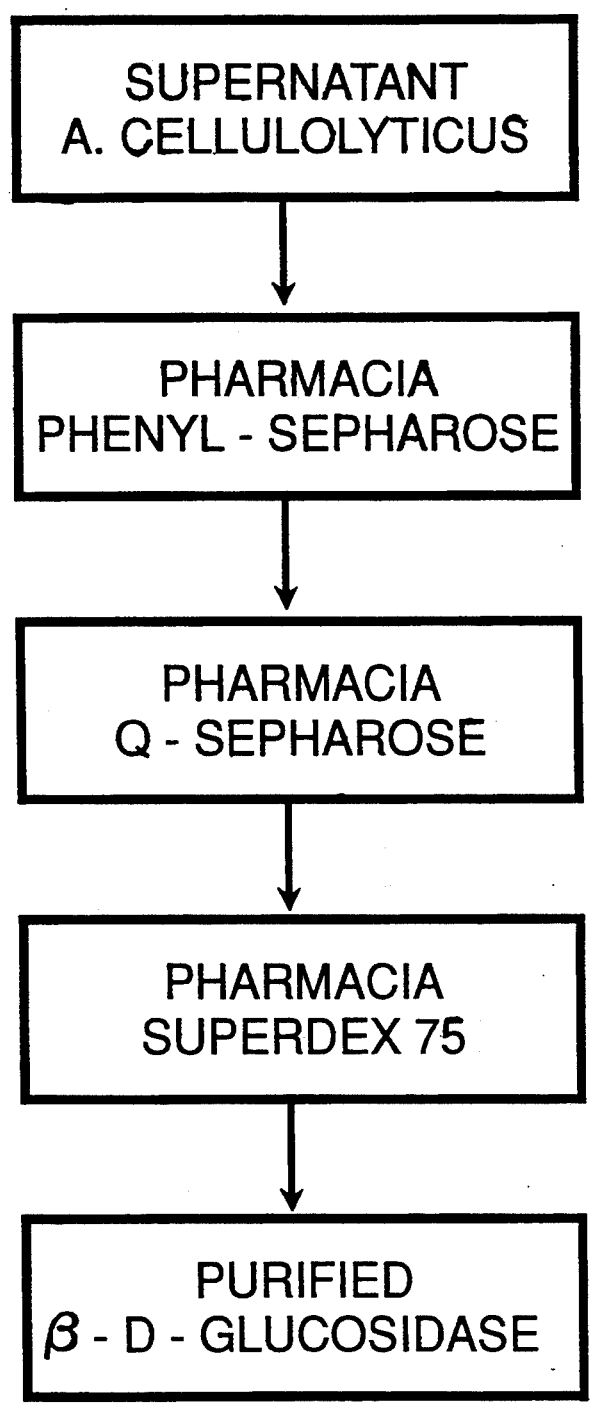
FIG. 1 is a flow-chart showing the isolation protocol used to purify the β-D-glucosidase from culture broth of *Acidophermus cellulolyticus*.
Figure 2C:
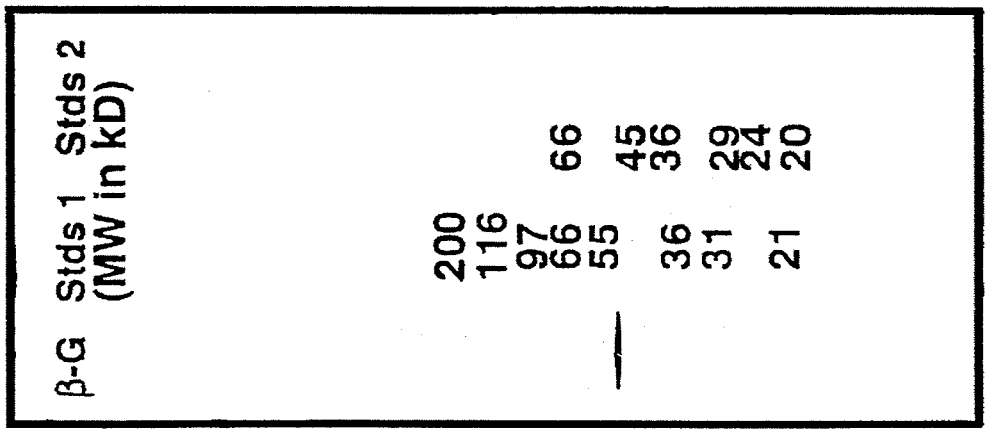
FIG. 2 shows the SDS-polyacrylamide gel electrophoresis (PAGE) profile of purified *Acidothermus cellulolyticus* β-D-glucosidase and two commercial preparations of standard proteins used for molecular weight determination. The single band shown for β-D-glucosidase shows purity.
Figure 2B:
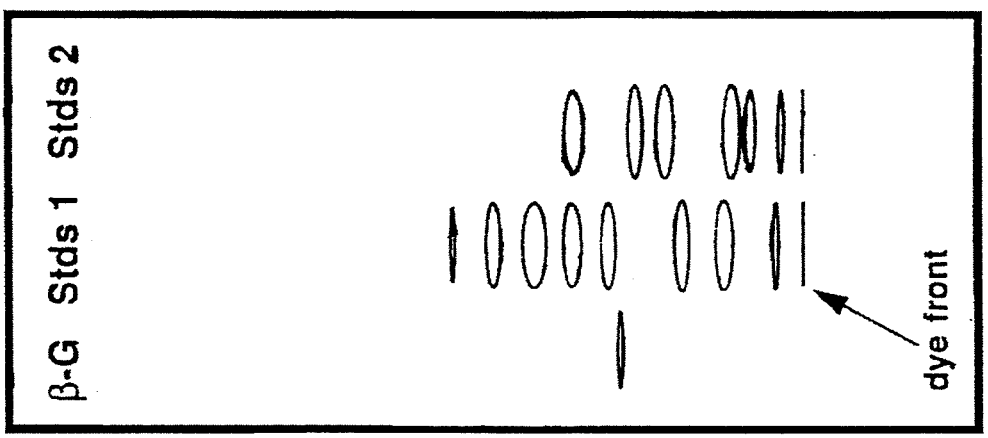
Figure 2A:
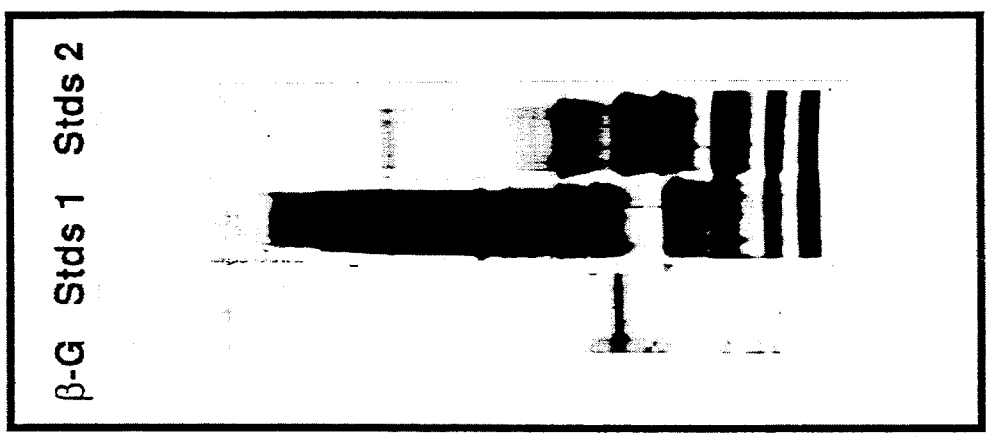
Figure 3:
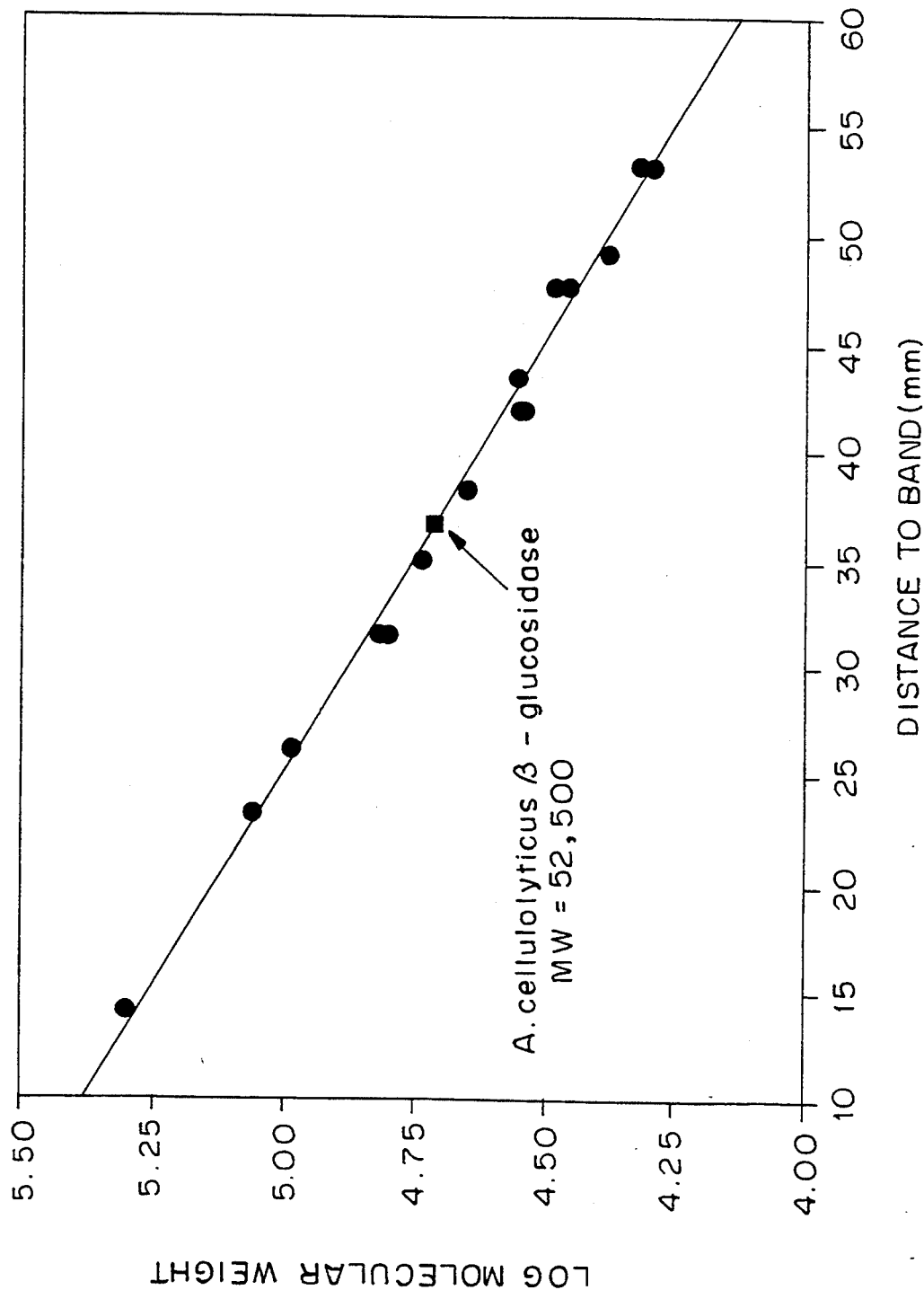
FIG. 3 shows the construction of a standard curve and the electrophoretic migration of the β-D-glucosidase enzyme from the data obtained in FIG. 2. The *Acidothermus cellulolyticus* β-D-glucosidase was found by SDS-PAGE to have a molecular weight of 52,500.
Figure 4:
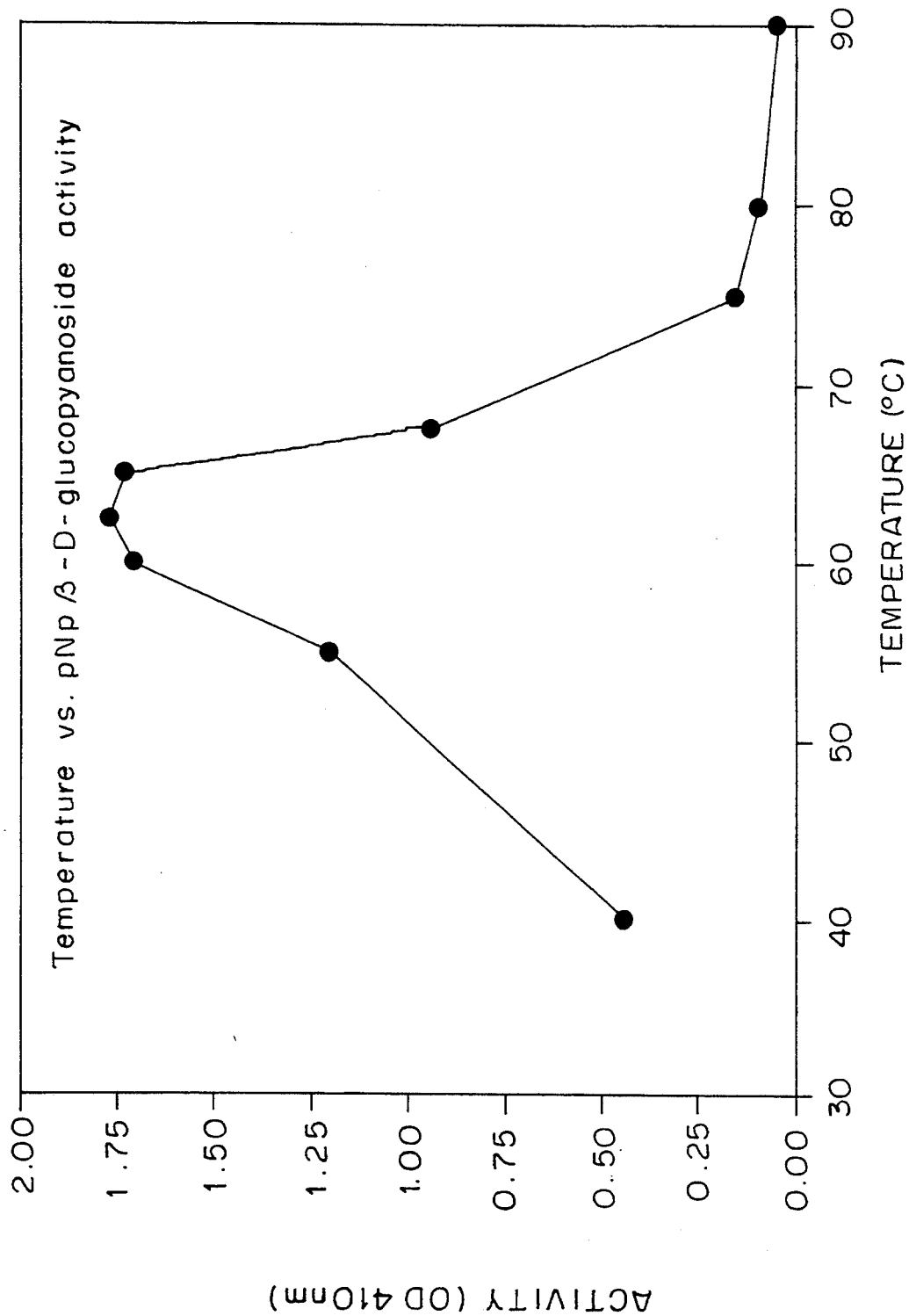
FIG. 4 shows the activity versus temperature profile for the β-D-glucosidase isolated from *Acidothermus cellulolyticus*. For these studies, the substrate pNP-β-D-glucopyranoside was used. Incubations were performed in 20 mM Tris pH 8.0 buffer and at the temperatures given for 30 minutes before assay. The optimum temperature for pNP-β-D-glucopyranoside activity is 65° C. The enzyme is nearly inactivated by incubation for 30 minutes or more at 80° C.

Purification of β-D-glucosidase from *Acidothermus cellulolyticus* culture broth Microorganism. *Acidothermus cellulolyticus* strain 11B was isolated from the upper Norris Geyser basin in Yellowstone National Park by Mohagheghi et al. 1986, *Int. J. System. Bacteriol.* 36:435–443 and has been deposited with the American Type Culture Collection, Rockville, Md. (ATCC #43068). The strain was maintained frozen at −70° C. after addition of 77 μL of dimethylsulfoxide per mL of culture suspension.

Culture media. The culture was prepared with an LPBM that contained the following, in grams per liter: $NH_4Cl$, 1.0; $KH_2PO_4$, 1.0; $Na_2HPO_4 \cdot 7H_2O$, 0.1; $MgSO_4 \cdot 7H_2O$, 0.2; and $CaCl_2 \cdot 2H_2O$, 0.2. The medium was also supplemented with the following, in g per L: yeast extract (Difco Laboratories, Detroit, Mich.) 1.0; D-cellobiose, 5.0 (unless noted otherwise) and 1.0% (v/v) Wolin trace mineral solution (11,12). Solka Floc BW-200 NF (James River Co., Berlin, N.H.) was used as the cellulosic substrate. All media were adjusted to pH 5.2 and sterilized by autoclaving.

Inoculum. A 1-mL aliquot of frozen culture was transferred immediately to a shake flask containing 20 mL of medium. After overnight incubation at 55° C. with rotary agitation, a 10-mL aliquot was transferred to a baffled shake flask containing 200 mL of medium. After growth under similar conditions, this inocula was transferred to small fermenters. Fermenters (Braun, Models Biostat V and Biostat S) of 1.0- or 2.5-L working volume were used. The medium was maintained at pH 5.2 during fermentation by the addition of 1.0 N $NH_4OH$ and 1.0 N $H_3PO_4$. The dissolved oxygen was maintained at 40% of saturation by increasing agitation rate and/or supplying pure oxygen as needed. The temperature was controlled at 55° C.

Fermentations. Inocula (2-L) from small fermenters were then used to initiate growth in a New Brunswick 150-L fermenter with a working volume of 120-L. Control and growth conditions were identical to that used for the second stage inoculum fermentations in 2-L fermenters, except that the fermenter was harvested after 36 h. Supernatant was freed from cells by continuous centrifugation using a CEPA model ZF-41 centrifuge equipped with cooling coils. The supernatant was concentrated by a factor of 20 using an Amicon model DC-2 hollow fiber ultraconcentrator. This concentrated supernatant was stored at 4° C.

Purification. The supernatant preparation was further concentrated (5×) using a small-scale ultrafiltration system (Amicon model HC-10). The sample was also dialyzed against 20 mM Tris buffer pH 8.0. An aliquot of this preparation was added to Tris buffer containing 1 M $(NH_4)_2SO_4$. This sample was loaded on an equilibrated Pharmacia Phenyl-Sepharose FPLC column at room temperature. After the column was washed with 5 volume of loading buffer, a reverse gradient (1-0M) in $(NH_4)_2SO_4$ was applied to the column. The β-D-Glucosidase activity eluted from the column at 0% $(NH_4)_2SO_4$. The fractions showing activity were then dialyzed against 20 mM Tris pH 8.0 buffer and loaded on an equilibrated Pharmacia Q-Sepharose FPLC column. This column was washed with loading buffer for 5–8 column volumes and subjected to a normal NaCl gradient (0–0.5M). The β-D-glucosidase activity was found to elute at a volume corresponding to a salt concentration of 660 mM NaCl. The enzyme eluted as a single, symmetrical peak, indicating a high level of homogeneity. These fractions were concentrated using an Amicon PM 10 membrane and loaded on a Pharmacia Superdex 75 size exclusion column. The purified protein was recovered from this column.

Characterization. The molecular weight as determined by SDS-PAGE and laser desorption mass spectrometry ranges from about 52,500 to about 52,100 daltons, respectively. The enzyme appears to aggregate in 20 mM acetate, 100 mM NaCl demonstrated by size-exclusion chromatography. The temperature optima for a 30 minute incubation was determined to be about 65° C. The $K_m$ was determined by classical Michaelis-Menten kinetics to be about 500 μM when pNP-β-D-glucoside is used as the substrate. This activity is equal to that of more commonly used enzymes, such as the β-D-glucosidase from *Aspergillus niger*. The activity profile on 6 commonly studied p-nitrophenyl substituted substrates shows that this enzyme has the highest activity of pNP-glucopyranoside, and thus is clearly a β-D-glucosidase.

EXAMPLE 2

| Characteristics of *Acidothermus cellulolyticus* β-D-Glucosidase. | |
|---|---|
| MW by SDS-PAGE | 52,500 ± 2,000 daltons |
| MW by Laser Desorption Mass Spectrometry | 52,100 ± 100 daltons |
| Temperature optimum | 65° C. |
| pH optimum @ 65° C. | 4.0–4.5 |
| Isoelectric pI | 4.1 |
| $K_m$ (pNPG) | 500 μM |
| N-terminal peptide | AVPPVAIYANDL--- |
| Amino acid composition: | |
| amino acid | % wt |
| asx | 11.5 |
| glx | 9.48 |
| ser | 4.94 |
| gly | 6.42 |
| his | 3.83 |
| arg | 10.7 |
| thr | 8.82 |
| ala | 7.91 |
| pro | 5.64 |
| tyr | 5.43 |
| val | 7.51 |
| met | 1.62 |
| ile | 5.11 |
| leu | 6.16 |
| phe | 4.97 |
| lys | 1.05 |
| Activity on selected substrates: | |
| pNP-D-xylopyranoside | -0- |
| pNP-α-D-mannopyranoside | -0- |
| pNP-β-D-lactopyranoside | 0.79 units/mg protein (units = μmol pNphenol released/min) |
| pNP-β-D-glucopyranoside | 6.6 units/mg protein |

| | |
|---|---|
| pNP-α-D-glucopyranoside | -0- |
| pNP-β-D-galactopyranoside | 2.1 units/mg protein |
| Phosphate sensitivity | yes, phosphate concentrations less than 50 mM. |
| Substrate inhibition, pNPG | yes, at concentrations greater than 2 mg/mL. |

The optimum temperature enzyme activity of 65° C. for the thermostable-β-D-glucosidase produced by the bacterium *Acidothermus cellulolyticus* is approximately 20° C. higher than the temperature optima exhibited by most other β-D-glucosidases. This fact provides the enzyme with great potential utility for use in enzymatic conversion of cellulosic biomass to sugars, especially where high cellulolytic processes are required.

While the pH range over which the enzyme of β-D-glucosidase from *Acidothermus cellulolyticus* is operable at the temperature optimum of about 65° C. is from about 2 to about 7, the preferred range is from about 3 to about 6. Most preferred is a pH range of from about 4.0 to about 4.5.

The molecular weight range of β-D-glucosidase from *Acidothermus cellulolyticus* as determined by a single band from SDS-PAGE is about 52,500 daltons, this enzyme was also subjected to laser desorption mass spectrometry from MW determinatioin. Results from a LAZERMAT Spectrometer found the maximum size fragmentation product from *A. cellulolyticus* β-D-glucosidase to be about 52,100 daltons.

It is clear from the foregoing examples that the cellulase produced from the different microorganism of *Acidothermus cellulolyticus* is an enzyme that is unique in composition, and shows different activity types from cellulase systems produced by other microorganisms (of the same activity type).

Further significance of the lower molecular weight β-D-glucosidase is that it is more readily cloned and therefore more valuable to industry.

What is claimed is:

1. A purified low molecular weight β-D-glucosidase from *Acidothermus cellulolyticus* ATCC 43068, said enzyme is water soluble, possesses activity against pNP-β-D-glucopyranoside, a high of degree of stability toward heat, and exhibits optimal temperature activity at about 65° C. at a pH range of from about 2 to about 7, an inactivation temperature of about 80° C. at a pH range of from about 2 to about 7 and a molecular weight of from about 50.5–54.5 kD as determined by SDS-PAGE.

2. The purified β-D-glucosidase of claim 1, wherein the pH range for the optimal temperature activity is from about 3 to about 6, and the pH range for the inactivation temperature is from about 3 to about 6.

3. The purified β-D-glucosidase of claim 1, wherein the pH range for the optimal temperature activity is from about 4.0 to about 4.5.

4. The purified β-D-glucosidase of claim 1, characterized by an N-terminal peptide of AVPPVAIYANDL- - -.

5. A method for production of the β-D-glucosidase of claim 1, comprising culturing said bacterium in a nutrient medium therefor, filtering crude β-D-glucosidase by ultrafiltration, separating low molecular weight ultrafiltrate fractions by size exclusion chromatography, adding a concentrated buffer to said low molecular weight fraction of β-D-glucosidase fraction, passing said low molecular weight fraction through an ion exchange column equilibrated against 20 mM-Tris pH 8.0 loading buffer, and recovering said low molecular weight β-D-glucosidase fraction by using a shallow gradient of an increasing ionic strength buffer that increases linearly from 0 to about 650 mM NaCl, until purified low molecular weight β-D-glucosidase fractions are eluted off at about 650 mM.

* * * * *